(12) United States Patent
Adams

(10) Patent No.: US 9,867,605 B2
(45) Date of Patent: Jan. 16, 2018

(54) ACCESS INSTRUMENTS TO EXTEND A SURGICAL WORKING CHANNEL

(71) Applicant: CHOICESPINE, LP, Knoxville, TN (US)

(72) Inventor: Alicia Adams, Knoxville, TN (US)

(73) Assignee: CHOICESPINE, LP, Knoxville, TN (US)

( * ) Notice: Subject to any disclaimer, the term of this patent is extended or adjusted under 35 U.S.C. 154(b) by 0 days.

(21) Appl. No.: 15/437,583

(22) Filed: Feb. 21, 2017

(65) Prior Publication Data

US 2017/0333023 A1    Nov. 23, 2017

Related U.S. Application Data

(63) Continuation of application No. PCT/US2016/033609, filed on May 20, 2016.

(51) Int. Cl.
*A61B 1/32* (2006.01)
*A61B 17/02* (2006.01)

(52) U.S. Cl.
CPC ...... *A61B 17/0293* (2013.01); *A61B 17/0218* (2013.01)

(58) Field of Classification Search
CPC ..... A61B 1/3132; A61B 1/3135; A61B 1/317; A61B 1/32; A61B 1/303; A61B 1/31; A61B 1/313; A61B 17/02; A61B 17/0206; A61B 17/0293; A61B 17/0218; A61B 2017/0256; A61B 17/3423; A61B 17/025; A61B 17/3439; A61B 2017/00261; A61B 2017/0262
See application file for complete search history.

(56) References Cited

U.S. PATENT DOCUMENTS

| | | | | |
|---|---|---|---|---|
| 2,474,857 A | * | 7/1949 | Newman | A61B 17/02 600/206 |
| 2,807,259 A | * | 9/1957 | Guerriero | A61B 1/32 600/215 |
| 3,384,078 A | * | 5/1968 | Gauthier | A61B 17/02 600/215 |
| 3,749,088 A | * | 7/1973 | Kohlmann | A61B 17/0293 403/107 |

(Continued)

OTHER PUBLICATIONS

Cho, Ki Yun, Written Opinion of the International Searching Authority for PCT/US2016/033609, dated Dec. 8, 2016, 5 pages, Korean Intellectual Property Office, Daejeon, South Korea.

(Continued)

*Primary Examiner* — Lynnsy Summitt
(74) *Attorney, Agent, or Firm* — Kevin E. Flynn; Flynn IP Law

(57) ABSTRACT

A channel retractor with one or more gate tracks to receive one or more slide gates to hold one or more extended retractors away from the surgical access channel running through the extended retractor. The distal ends of the one or more extended retractors held by the one or more slide gates holding tissue distal to the end of the channel retractor to maintain an extended access channel beyond the distal end of the channel retractor. The channel retractor assembly may be used to hold open an extended access channel through the psoas muscle to allow access to the spine or through other tissue in other surgical access techniques.

7 Claims, 11 Drawing Sheets

(56) References Cited

U.S. PATENT DOCUMENTS

| | | | | |
|---|---|---|---|---|
| 4,616,635 A * | 10/1986 | Caspar | A61B 17/02 | 600/215 |
| 4,909,789 A * | 3/1990 | Taguchi | A61B 17/0218 | 604/107 |
| 5,183,464 A * | 2/1993 | Dubrul | A61M 25/0023 | 604/104 |
| 5,571,109 A * | 11/1996 | Bertagnoli | A61B 17/025 | 606/86 A |
| 5,928,139 A * | 7/1999 | Koros | A61B 17/0206 | 600/205 |
| 5,976,146 A * | 11/1999 | Ogawa | A61B 17/00234 | 604/174 |
| 6,139,493 A * | 10/2000 | Koros | A61B 17/0206 | 600/213 |
| 6,371,968 B1 * | 4/2002 | Kogasaka | A61B 17/00234 | 600/201 |
| 6,951,538 B2 * | 10/2005 | Ritland | A61B 17/1757 | 600/210 |
| 7,150,714 B2 * | 12/2006 | Myles | A61B 17/0293 | 600/205 |
| 7,374,534 B2 * | 5/2008 | Dalton | A61B 17/0218 | 600/222 |
| 7,879,009 B1 * | 2/2011 | Haddock | A61B 1/32 | 600/210 |
| 8,048,109 B2 * | 11/2011 | Garcia-Bengochea | A61B 17/02 | 600/208 |
| 8,105,236 B2 * | 1/2012 | Malandain | A61B 90/35 | 600/206 |
| 8,568,306 B2 * | 10/2013 | Hardenbrook | A61B 17/0206 | 600/210 |
| 8,764,757 B1 * | 7/2014 | Tumialan | A61F 2/4455 | 600/210 |
| 8,795,167 B2 * | 8/2014 | Ainsworth | A61B 17/0642 | 600/222 |
| 8,801,608 B2 | 8/2014 | Hardenbrook | | |
| 9,131,933 B2 * | 9/2015 | Mire | A61B 17/02 | |
| 9,380,932 B1 * | 7/2016 | Lynn | A61B 1/32 | |
| 9,615,818 B2 * | 4/2017 | Baudouin | A61B 17/0206 | |
| 9,655,505 B1 * | 5/2017 | Gharib | A61B 1/32 | |
| 9,675,334 B2 * | 6/2017 | Heiges | A61B 17/0218 | |
| 9,737,288 B2 * | 8/2017 | Karpowicz | A61B 17/0206 | |
| 9,795,367 B1 * | 10/2017 | Lee | A61B 17/0206 | |
| 2002/0022771 A1 * | 2/2002 | Diokno | A61B 1/32 | 600/220 |
| 2002/0115910 A1 * | 8/2002 | Diokno | A61B 1/32 | 600/220 |
| 2002/0156433 A1 * | 10/2002 | Le Huec | A61B 17/0218 | 604/264 |
| 2003/0212309 A1 * | 11/2003 | Dietzel | A61B 1/267 | 600/190 |
| 2004/0024291 A1 | 2/2004 | Zinkel | | |
| 2005/0021069 A1 * | 1/2005 | Feuer | A61B 1/303 | 606/192 |
| 2005/0075540 A1 * | 4/2005 | Shluzas | A61B 1/00149 | 600/203 |
| 2005/0137461 A1 * | 6/2005 | Marchek | A61B 17/025 | 600/220 |
| 2005/0159651 A1 * | 7/2005 | Raymond | A61B 17/02 | 600/213 |
| 2005/0245942 A1 * | 11/2005 | DiPoto | A61B 17/3439 | 606/108 |
| 2006/0129033 A1 * | 6/2006 | Frasier | A61B 1/32 | 600/215 |
| 2006/0142642 A1 * | 6/2006 | Lins | A61B 1/32 | 600/210 |
| 2006/0200186 A1 * | 9/2006 | Marchek | A61B 17/0218 | 606/191 |
| 2006/0229636 A1 * | 10/2006 | Woodburn, Sr. | A61B 17/02 | 606/108 |
| 2006/0229656 A1 * | 10/2006 | McDonnell | A61M 29/00 | 606/191 |
| 2006/0247645 A1 * | 11/2006 | Wilcox | A61B 17/025 | 606/86 R |
| 2006/0264706 A1 * | 11/2006 | Piskun | A61B 1/31 | 600/105 |
| 2007/0038034 A1 * | 2/2007 | Sweeney, II | A61B 17/02 | 600/219 |
| 2007/0038216 A1 * | 2/2007 | Hamada | A61B 17/02 | 606/53 |
| 2007/0060939 A1 * | 3/2007 | Lancial | A61B 1/00154 | 606/191 |
| 2007/0100366 A1 * | 5/2007 | Dziedzic | A61B 17/02 | 606/191 |
| 2007/0203399 A1 * | 8/2007 | Gephart | A61B 1/32 | 600/219 |
| 2007/0208227 A1 * | 9/2007 | Smith | A61B 1/313 | 600/219 |
| 2007/0208228 A1 | 9/2007 | Pavento | | |
| 2007/0208229 A1 * | 9/2007 | Prusmack | A61B 1/32 | 600/234 |
| 2007/0270866 A1 * | 11/2007 | von Jako | A61B 17/02 | 606/86 R |
| 2007/0276191 A1 * | 11/2007 | Selover | A61B 1/06 | 600/245 |
| 2008/0021285 A1 * | 1/2008 | Drzyzga | A61B 1/32 | 600/215 |
| 2008/0147109 A1 * | 6/2008 | Kambin | A61B 17/0218 | 606/190 |
| 2008/0188759 A1 * | 8/2008 | Saadat | A61B 1/0008 | 600/478 |
| 2009/0005646 A1 * | 1/2009 | Nowitzke | A61B 17/0218 | 600/187 |
| 2009/0018400 A1 | 1/2009 | Raymond | | |
| 2009/0143640 A1 * | 6/2009 | Saadat | A61B 1/00089 | 600/104 |
| 2009/0149857 A1 * | 6/2009 | Culbert | A61B 1/018 | 606/80 |
| 2009/0287061 A1 * | 11/2009 | Feigenbaum | A61B 17/3423 | 600/204 |
| 2009/0306586 A1 * | 12/2009 | Ross | A61B 17/3439 | 604/93.01 |
| 2010/0076502 A1 * | 3/2010 | Guyer | A61B 17/02 | 606/86 R |
| 2010/0145148 A1 * | 6/2010 | Wenchell | A61B 1/0008 | 600/115 |
| 2010/0217088 A1 * | 8/2010 | Heiges | A61B 17/3439 | 600/207 |
| 2010/0228095 A1 * | 9/2010 | Warren | A61B 1/32 | 600/210 |
| 2010/0240961 A1 * | 9/2010 | Aferzon | A61B 1/32 | 600/212 |
| 2011/0034779 A1 * | 2/2011 | Louftus | A61B 17/0206 | 600/210 |
| 2011/0040154 A1 * | 2/2011 | Reznik | A61B 17/3421 | 600/227 |
| 2011/0130793 A1 * | 6/2011 | Woolley | A61B 17/0206 | 606/279 |
| 2011/0196208 A1 * | 8/2011 | Warren | A61B 1/32 | 600/210 |
| 2011/0237898 A1 | 9/2011 | Stone | | |
| 2011/0245618 A1 * | 10/2011 | Fenster | A61B 1/303 | 600/203 |
| 2011/0276139 A1 | 11/2011 | Mahoney | | |
| 2012/0010471 A1 * | 1/2012 | Mire | A61M 29/00 | 600/210 |
| 2012/0016204 A1 * | 1/2012 | Bastia | A61B 1/00108 | 600/245 |
| 2012/0022575 A1 * | 1/2012 | Mire | A61B 5/4893 | 606/198 |
| 2012/0130161 A1 * | 5/2012 | Lauryssen | A61B 17/3439 | 600/104 |
| 2012/0232349 A1 * | 9/2012 | Perrow | A61B 1/32 | 600/201 |
| 2012/0289816 A1 * | 11/2012 | Mark | A61M 39/0247 | 600/411 |
| 2012/0323080 A1 * | 12/2012 | DeRidder | A61B 1/32 | 600/208 |

(56) References Cited

U.S. PATENT DOCUMENTS

| | | | | |
|---|---|---|---|---|
| 2013/0006061 A1* | 1/2013 | Alexander | A61B 1/32 | 600/235 |
| 2013/0102850 A1* | 4/2013 | Fiorella | A61B 1/04 | 600/210 |
| 2013/0103103 A1* | 4/2013 | Mire | A61B 1/32 | 606/86 A |
| 2013/0109910 A1* | 5/2013 | Alexander | A61B 17/00234 | 600/37 |
| 2013/0137932 A1* | 5/2013 | Piech | A61B 1/32 | 600/204 |
| 2013/0190558 A1* | 7/2013 | Alexander | A61B 1/32 | 600/37 |
| 2013/0190571 A1* | 7/2013 | Chen | A61B 17/24 | 600/204 |
| 2013/0281791 A1* | 10/2013 | Aferzon | A61B 1/06 | 600/245 |
| 2014/0052018 A1* | 2/2014 | Hawkins | A61B 10/02 | 600/562 |
| 2014/0114341 A1* | 4/2014 | Wolff | A61M 29/00 | 606/198 |
| 2014/0128979 A1 | 5/2014 | Womble | | |
| 2014/0135584 A1* | 5/2014 | Lee | A61B 17/0206 | 600/202 |
| 2014/0171747 A1* | 6/2014 | Roeloffs | A61B 1/32 | 600/220 |
| 2014/0323811 A1* | 10/2014 | DeSantis | A61B 1/06 | 600/213 |
| 2014/0350347 A1* | 11/2014 | Karpowicz | A61B 17/0206 | 600/215 |
| 2015/0080973 A1* | 3/2015 | Eastlack | A61F 2/4455 | 606/86 A |
| 2015/0094533 A1* | 4/2015 | Kleiner | A61B 1/0607 | 600/109 |
| 2015/0164552 A1* | 6/2015 | Chen | A61B 17/3423 | 600/204 |
| 2015/0190128 A1* | 7/2015 | Fenn | A61B 1/018 | 600/202 |
| 2015/0305731 A1* | 10/2015 | Friedrich | A61B 90/30 | 600/216 |
| 2015/0351738 A1* | 12/2015 | Perrow | A61B 17/0293 | 600/226 |
| 2015/0366552 A1* | 12/2015 | Sasaki | A61B 17/0293 | 600/210 |
| 2016/0051243 A1* | 2/2016 | Heiges | A61B 17/0218 | 600/204 |
| 2016/0081818 A1* | 3/2016 | Waugh | A61B 17/0206 | 623/17.16 |
| 2016/0192922 A1* | 7/2016 | Friedrich | A61B 17/0206 | 600/214 |
| 2017/0143325 A1* | 5/2017 | Lynn | A61B 17/0218 | |
| 2017/0150958 A1* | 6/2017 | Sasaki | A61B 17/0218 | |
| 2017/0156580 A1* | 6/2017 | Miles | A61B 1/32 | |
| 2017/0156716 A1* | 6/2017 | Sandhu | A61B 17/0218 | |
| 2017/0156814 A1* | 6/2017 | Thommen | A61B 90/03 | |
| 2017/0172558 A1* | 6/2017 | Miles | A61B 17/0218 | |
| 2017/0258315 A1* | 9/2017 | Gharib | A61B 1/32 | |
| 2017/0333021 A1* | 11/2017 | Heiges | A61M 29/00 | |

OTHER PUBLICATIONS

Cho, Ki Yun, International Search Report of the International Searching Authority for PCT/US2016/033609, dated Dec. 8, 2016, 3 pages, Korean Intellectual Property Office, Daejeon, South Korea.

* cited by examiner

— 1 —

ACCESS INSTRUMENTS TO EXTEND A SURGICAL WORKING CHANNEL

This application claims priority and incorporates by reference commonly assigned and copending PCT Application No. PCT/US2016/033609 for Access Instrument To Extend A Surgical Working Channel filed on May 20, 2016.

BACKGROUND

Field of the Disclosure

This disclosure relates generally to minimally invasive surgical techniques including techniques and implants for provision of therapy to a spine from a lateral approach. Implants that may be used with other approaches to the spine are disclosed. Minimally invasive surgical techniques using one or more extended retractors to create an extended access route such as the non-limiting example of lateral access to the spine are disclosed.

This application builds upon the concepts expressed in U.S. Pat. No. 8,795,167 B2 issued Aug. 5, 2014 for Spinal Therapy Lateral Approach Access Instruments. The contents of the '167 are incorporated by reference herein.

General Comments and Terminology

In the context of the present disclosure, as used herein the term "assembly" refers to implants, instruments and instruments systems which are configured to comprise multiple components, which may or may not be contiguous. It is further understood that individual components may themselves be configured as sub-assemblies, e.g., comprising a plurality of component materials, and that the formation of the components may involve intermediate processes or appliances.

It will also be understood that upon formation of assemblies from multiple components and deployment, individual components of the present disclosure may or may not remain as discernibly distinct. It will also be understood that, for convenience, system components may be packaged and provided either individually, or as in "kits," and either as reusable or disposable.

As used herein, the term "biocompatible" refers to an absence of chronic inflammation response or cytotoxicity when or if physiological tissues are in contact with, or exposed to (e.g., wear debris) the materials and devices of the present disclosure. In addition to biocompatibility, in another aspect of the present disclosure it is preferred that the materials comprising the instrument systems are sterilizable.

In one aspect of the present disclosure, certain components of the device assemblies and systems of the present disclosure are configured to comprise biocompatible materials and are able to withstand, without wear, multiple cycles/procedures without failing. It will be further understood that the length and dimensions of instruments and components described herein will depend in part on the target site selection of the treatment procedure and the physical characteristics of the patient, as well as the construction materials and intended functionality, as will be apparent to those of skill in the art In order to make it easier for a reader to find certain sections of this document that are of particular interest to the reader, a series of headings have been used. These headings are solely for the purpose of helping readers navigate the document and do not serve to limit the relevance of any particular section to exclusively the topic listed in the heading.

In the context of this discussion: anterior refers to in front of the spinal column; (ventral) and posterior refers to behind the column (dorsal); cephalad refers to the direction or location that is closer to the patient's head (sometimes "superior"); caudal (sometimes "inferior") refers to the direction or location that is closer to the feet. Proximal is closer to the beginning of the channel and thus the surgeon; distal is further from the beginning of the channel and in use more distant from the surgeon. When referencing tools including cutters or other tools distal would be the end intended for insertion into the access channel and proximal refers to the other end, generally the end closer to the handle for the tool.

The sequence of operations (or steps) is not limited to the order presented in the claims or figures unless specifically indicated otherwise.

Prior Art

Earlier work by one of the co-inventors of the current application discloses a minimally invasive surgical technique that may be used to traverse the psoas muscle to form an access channel to the lateral side of lumbar disc spaces. This earlier work resulted in U.S. Pat. No. 8,795,167 for Spinal Therapy Lateral Approach Access Instruments. The '167 patent is hereby incorporated by reference in its entirety.

The '167 showed a number of access tools and implants. The implants are not relevant to the present disclosure and will not be further discussed. In order to understand the advantages of the present disclosure, it is useful to review the first embodiment of an access system disclosed in the '167.

FIG. 1 shows an example of a channel retractor 164. Note that the channel retractor 164 may have a substantially uniform cross section (as taken with respect to the longitudinal axis). The cross section of the channel retractor 164 may be round (uniform radius), elliptical, square, oblong, or other shapes. In many instances the cross section will have rounded surfaces even for shapes such as a square or rectangle that is longer than it is wide. The cross section of the channel retractor 164 in FIG. 1 may be described as a rounded rectangle as it has a pair of curved ends separated by straight walls. The channel retractor 164 is sometimes called a tubular retractor as it comprises a lumen that is an opening at a proximal end 212 extending throughout its length to an opening at a distal end 216, the channel retractor 164 thus having an inner perimeter 206. The channel retractor 164 may have a stabilizer arm 168 for use to connect to a table mounted retractor arm.

Creating an Opening in the Psoas Muscle.

To prepare for work on the psoas muscle, it may be useful to add lighting. One way to add lighting is to plug one end of a fiber optic cable into a light source in accordance with manufacturer's instructions. The other end of the fiber optic cable may be attached to a stadium mount light. The stadium mount light may then be attached to the proximal end of the channel retractor 164 so that the outer surface of the psoas muscle near the distal end of the channel retractor 164 is well lit. The proximal end of the channel retractor 164 may be adapted to allow the surgeon a choice of several locations for mounting the stadium mount light to the channel retractor 164.

As nerves are in the psoas muscle and care is taken to avoid damaging the nerves, those of skill in the art understand the process of neuromonitoring to locate the positioning of the nerves. As neuromonitoring is not the focus of the present application, details on the process of neuromonitoring are not included here.

The top surface of the psoas muscle is split between the muscle fibers typically using a Penfield dissector or a Cobb dissector. Some surgeons may prefer a straight dissector, and some may prefer an angled dissector. FIG. 2 shows an angled Cobb dissector 176 that may be used. The angled Cobb dissector 176 has a set of insertion depth markings 180 that may be used as an input by the surgeon to select components of the appropriate length for secondary retraction steps.

After the psoas muscle is split, some surgeons will choose to insert a 90 degree nerve retractor down the side of the dissector used to maintain the split in the psoas muscle.

A guide pin (not shown) may be inserted along the nerve retractor (or dissector) through the split in the psoas muscle into the interior of the targeted disc space. The distal end of the guide pin may be inserted five to ten millimeters into the disc space. Once the guide pin is positioned, the nerve retractor may be removed from the incision.

A lateral fluoroscopy image may be taken to confirm that the guide pin is in the anterior/posterior center of the disc space. If the guide pin is properly positioned, an A/P fluoroscopic view may be used to confirm that the channel retractor 164 is centered over the guide pin. Once the channel retractor 164 position has been adjusted to be centered over the centered guide pin, the guide pin may be removed.

Creating an Access Channel in the Psoas Muscle.

Enlarging the small opening created by the initial opening in the tough fibrous psoas muscle is challenging. The enlargement may be performed after the channel retractor 164 is properly aligned and provides a working channel from outside the patient to the edge of the psoas muscle. However, sufficient force needs to be applied to expand the psoas muscle and then the enlarged opening in the psoas muscle should be maintained as a working channel to the disc space to allow for the surgical procedure on the disc, such as a fusion procedure.

One way to achieve the task of opening the psoas muscle and maintaining the access channel is to use a tube in a tube assembly as taught in U.S. Pat. No. 8,795,167.

Tube in a Tube.

FIG. 3 to FIG. 7 illustrate the concept of a tube in a tube secondary retraction system. In FIG. 3, a cross section of a channel retractor 204 is shown. Channel retractor 204 has a circular rather than rounded rectangular cross section, other designs taught in the '167 included rounded rectangular shaped retractors. The channel retractor 204 has a closed inner perimeter that defines a working channel 208 through a first tissue from the proximal end 212 outside the patient to a distal end 216 placed adjacent to the edge of a second tissue such as the psoas muscle.

FIG. 4 shows the cross section of FIG. 3 after the distal end portion 232 of a first extended retractor 236 is moved through the channel retractor 204 and into the opening made in the psoas muscle as described above.

FIG. 5 shows the cross section of FIG. 4 after a distal end portion 224 of a second extended retractor 228 is moved through the channel retractor 204 and into the opening made in the psoas muscle. Notice that the first extended retractor 236 and second extended retractor 228 each have a first angle 240 between the distal end portion 224, 232 for insertion into the psoas muscle and the intermediate portion 248 for traversing the channel retractor 204. The intermediate portion 248 may be called the channel retractor portion. This obtuse first angle 240 allows the two distal end portions 224 and 232 to be substantially aligned for placement adjacent to one another in an opening in the psoas muscle. The first extended retractor 236 and the second extended retractor 228 each have a second angle 256 of approximately ninety degrees for placement at the proximal end 212 of the channel retractor 204 to allow a handle portion 260 for the first extended retractor 236 and second extended retractor 228 to be out of the way of the surgeon, so the surgeon can easily have direct visualization of the psoas muscle.

FIG. 6 illustrates inserting an inner sleeve 356 into the channel retractor 204 to force the first extended retractor 236 and second extended retractor 228 to substantially opposite sidewall portions of the inner perimeter 206 of the channel retractor 204 to gradually and controllably spread the opening in the psoas muscle. In the most basic form (not shown here) the inner sleeve could be an appropriately sized hollow cylinder. The '167 showed embodiments of the inner sleeve that were U-shaped rather than a fully closed perimeter of a cylinder.

Note that the inner sleeve 356 has a retractor receiving indentation 360 that is visible in this view. A corresponding retractor receiving indentation is on the opposite side. The distal end of the inner sleeve 356 may include a bevel 368.

FIG. 7 is a top perspective view during insertion of the inner sleeve 356 to form an assembly with portions of the first extended retractor 236 and second extended retractor 228 sandwiched between the inner sleeve 356 and the inner perimeter 206 of the channel retractor 204. Note that the first extended retractor 236 and the second extended retractor 228 may be inserted to different depths. For example, the extended retractor placed on the anterior side of the opening in the psoas muscle may need to extend further distally than the extended retractor placed on the posterior side of the opening in the psoas muscle, due to anatomical differences of the spine.

One of skill in the art will appreciate that an inner sleeve may be sized to push the first extended retractor and the second extended retractor outward from the centerline of the channel retractor, but not far enough to move both the extended retractors against the inner perimeter of the channel retractor. Some surgeons may prefer a smaller expansion of the second tissue and thus may not opt to fully expand the tissue. Conversely, a surgeon may opt for an initial partial expansion followed by a second expansion to push the extended retractors all the way to the inner perimeter of the channel retractor.

Notches 324 in the distal end 216 of the channel retractor 204 allow the distal end portions 224 and 232 of the extended retractors 228 and 236 to extend beyond the inner perimeter 206 of the channel retractor 204 when the extended retractors 228 and 236 are positioned elevated relative to a proximal face 316 of channel retractor 204.

One of skill in the art will recognize that at the process step illustrated in FIG. 6, there are four primary components, channel retractor 204, inner sleeve 356, and extended retractors 228 and 236. While the channel retractor may be secured with the table mounted retractor arm with a stabilization arm after being advanced distally down to the psoas muscle, this still leaves three primary components that are not fastened to anything as of the process step shown in FIG. 6. Three components are difficult to manage by one surgeon with only two hands. Having additional people hold one or more components is certainly possible but facilitating the process so that one person can handle the application of force to move the distal ends of the extended retractors would be an improvement to the prior art.

SUMMARY OF THE DISCLOSURE

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Some of the teachings of the present disclosure may be summarized as an assembly for maintaining an extended access channel in tissue, the assembly having a channel retractor with a first gate track to receive a slide gate to press an extended retractor radially outward relative to the longitudinal centerline of the lumen such that when the first extended retractor has the distal portion extending beyond the distal end of the channel retractor and retaining tissue to provide the extended access channel inserting the first slide gate into the first gate track causes the distal portion of the first extended retractor to remain separated from the longitudinal centerline of the lumen to maintain the extended access channel.

Other teachings of the present disclosure include having a channel retractor that has at least one tab gap in a proximal face of the channel retractor to receive a corresponding tab from the first slide gate when the first slide gate is fully inserted into the first gate track so that a surgeon may subsequently pull on a distal face of the tab to remove the first slide gate from the channel retractor.

Other teachings of the present disclosure may be summarized as having a channel retractor with a second gate track to receive a slide gate to press a second extended retractor radially outward relative to the longitudinal centerline of the lumen within the channel retractor; such that when the first extended retractor and the second extended retractor have at least parts of their distal portions extending beyond a distal end of the channel retractor and inserted into an opening in tissue, inserting the first slide gate and second slide gates into the first gate track and second gate track causes the distal portions of the first extended retractor and the second extended retractor to remain separated from the longitudinal centerline of the lumen which may be used to maintain the opening in tissue distal to the distal end of the channel retractor.

The present disclosure teaches that the second slide gate may be located opposite from the first slide gate but is not required to be opposite. There may be more than two slide gates.

Some of the teachings of the present disclosure may be summarized as a method of providing an extended access channel to a portion of a spine of a patient for an extended access channel that traverses a path that was originally obstructed by a psoas muscle. The method includes:
  creating an access channel from outside the patient to the psoas muscle;
  placing a channel retractor to maintain the access channel from outside the patient to the psoas muscle;
  anchoring the channel retractor so that the channel retractor is immobile;
  moving psoas tissue located distal to a distal end of the channel retractor away from a longitudinal centerline of the channel retractor with a distal end of a first extended retractor to create the extended access channel; and
  retaining the psoas tissue away from a longitudinal centerline of the channel retractor with a first slide gate inserted into a first gate track integral to a first portion of an inner wall of the channel retractor to hold an intermediate portion of the first extended retractor against the first portion of the inner wall of the channel retractor to maintain the extended access channel to the portion of the spine of the patient.

The teachings of the present disclosure include both splitting the psoas and using a pair of retained extended retractors to maintain the extended access channel and using a single extended retractor to sweep tissue across the access channel and then retain the tissue with a single extended retractor.

The teachings of the present disclosure are not limited to use to extend an access channel across a psoas muscle to reach the spine. Other tissue may be retained by one, two, three or even more extended retractors for other surgical techniques. Thus the concept may be expressed as a method of providing an extended access channel through tissue.
  creating an access channel from outside a patient to a first depth in the patient;
  placing a channel retractor to maintain the access channel from outside the patient to the first depth;
  anchoring the channel retractor so that the channel retractor is immobile;
  moving tissue located distal to a distal end of the channel retractor away from a longitudinal centerline of the channel retractor with a distal end of a first extended retractor to create the extended access channel; and
  retaining the tissue away from a longitudinal centerline of the channel retractor with a first slide gate inserted into a first gate track integral to a first portion of an inner wall of the channel retractor to hold an intermediate portion of the first extended retractor against the first portion of the inner wall of the channel retractor to maintain the extended access channel.

The method may further include moving additional tissue located distal to the distal end of the channel retractor away from the longitudinal centerline of the channel retractor with a distal end of a second extended retractor; and retaining the additional tissue away from the longitudinal centerline of the channel retractor with a second slide gate inserted into a second gate track integral to a second portion of the inner wall of the channel retractor to hold an intermediate portion of the second extended retractor against the second portion of the inner wall of the channel retractor to maintain the extended access channel.

The second gate track is located directly across from the first gate track such that the second slide gate holds the second extended retractor directly across from the first slide gate with the held first extended retractor but this is not required.

There may be more than two extended retractors and slide gates engaged with a corresponding number of gate tracks.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

Other systems, methods, features and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

DETAILED DESCRIPTION

Figure 1:
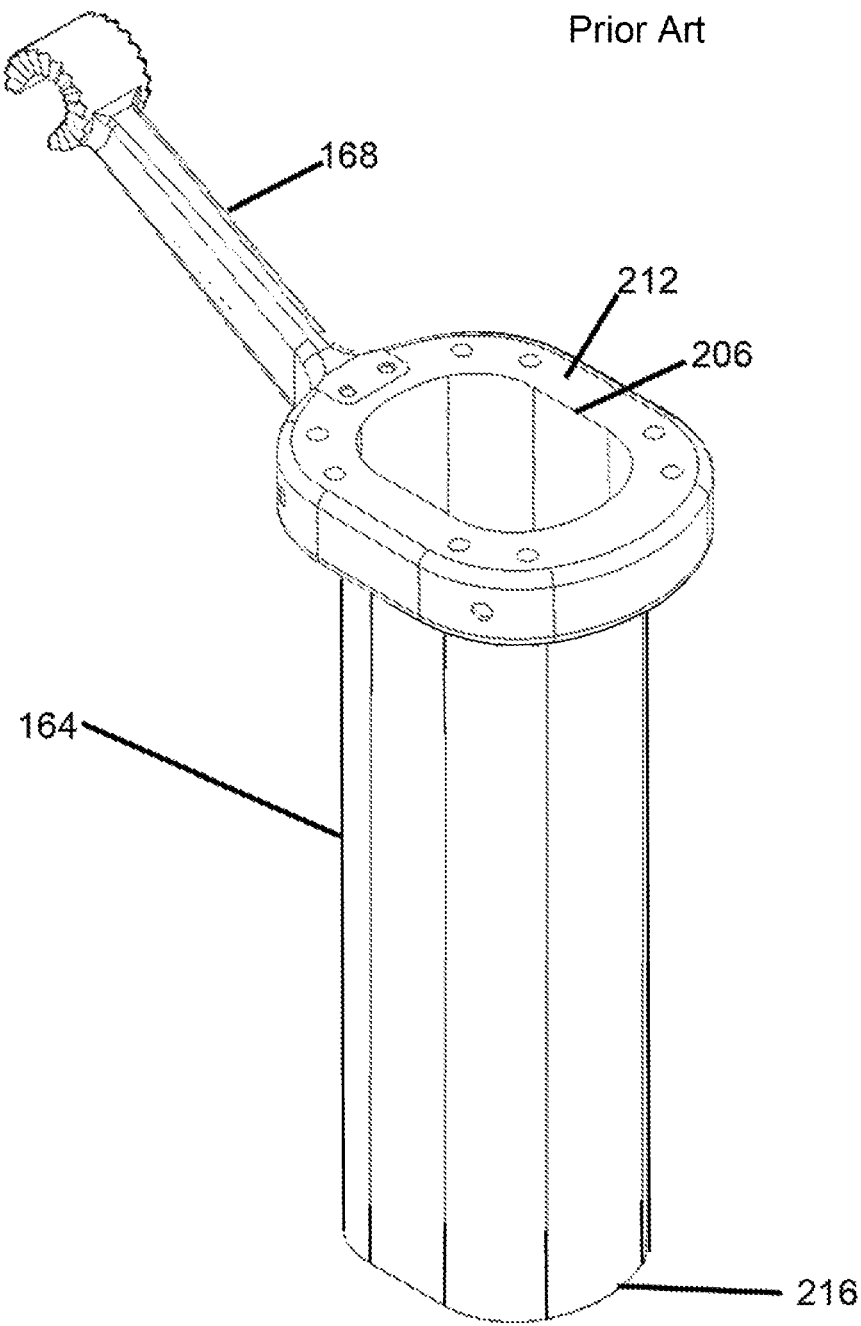
FIG. 1 is a top perspective view of a channel retractor from the prior art.
Figure 2:
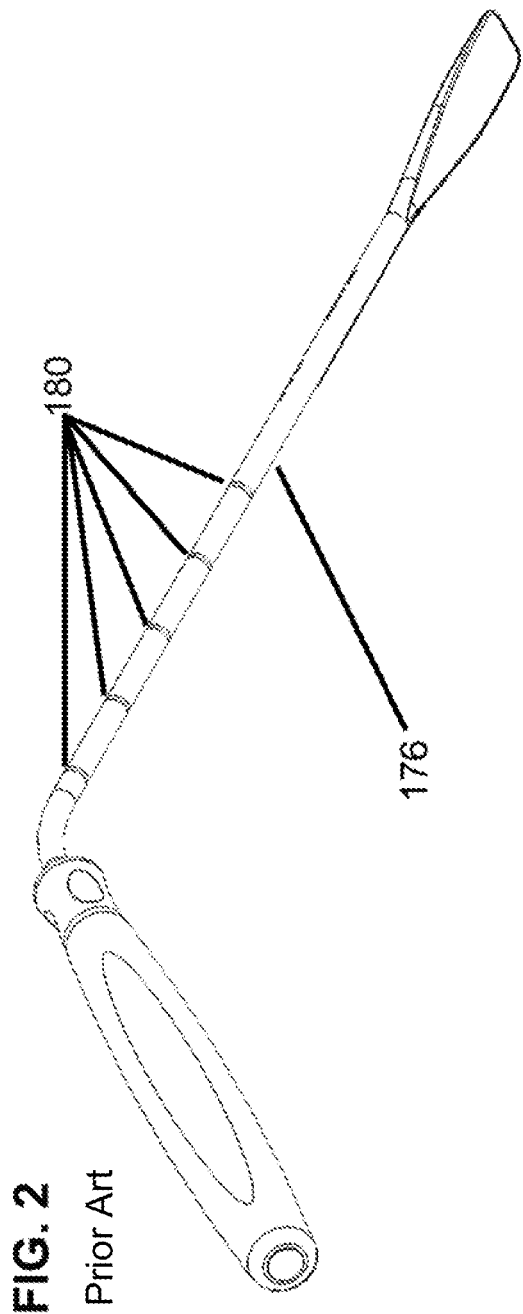
FIG. 2 is an angled Cobb dissector from the prior art.
Figure 3:
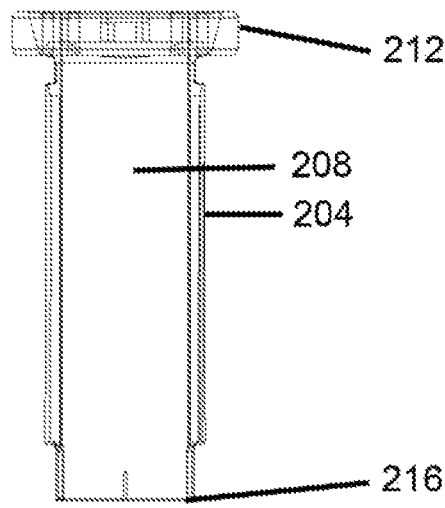
FIG. 3 is a cross section of a channel retractor from the prior art.
Figure 4:
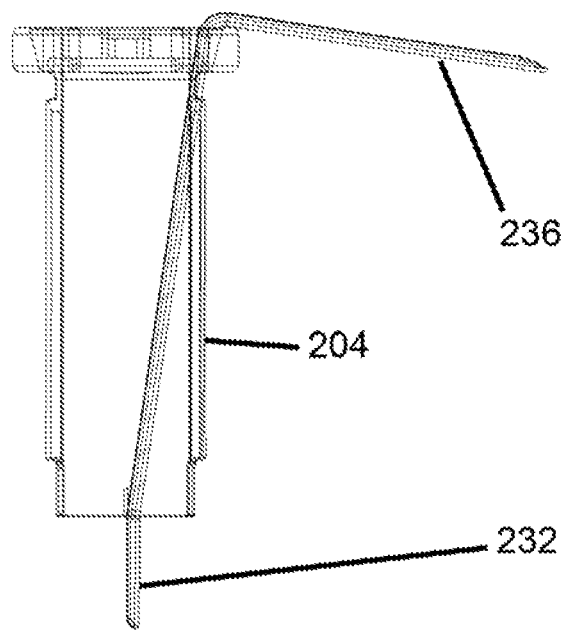
FIG. 4 is a cross section of a channel retractor with an extended retractor from the prior art.
Figure 5:
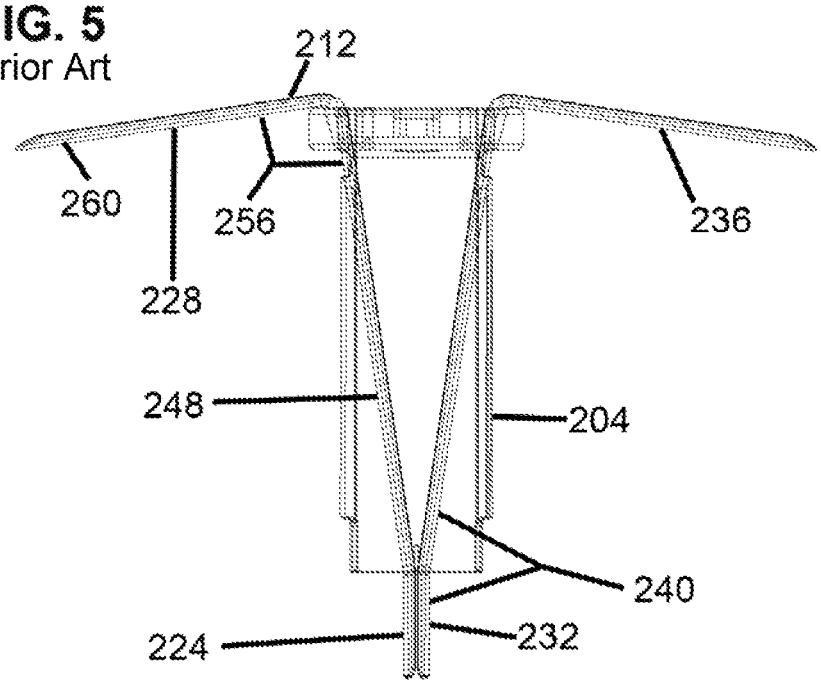
FIG. 5 is a cross section of a channel retractor with two extended retractors from the prior art.

The present application has a range of teachings that may be used to advantage in a number of settings. However, to provide these teachings with clarity, it is useful to describe one use of many of the teachings in great detail. The use described below is to access a lateral portion of a human spine using a lateral approach in order to provide therapy such as a fusion procedure to a vertebral motion segment. This process may be broken down to a natural sequence of:
  Positioning the patient,
  Creating an access channel to the psoas muscle
  Creating an opening through the psoas muscle
  Enlarging an access channel through the psoas muscle.
  Preparing the disc space
  Delivering an implant which may include fusion promoting materials.
  Closing the access path.
Psoas Muscle.

The psoas muscle is a major muscle in the human body used to stabilize the base of the spine. The psoas muscle is involved in hip flexion and rotation. The psoas muscle runs on both lateral sides of the lumbar spine. The psoas muscle is of interest for spine surgery in that this tough muscle must be traversed to access lumbar discs from a lateral approach.

Positioning the Patient.

Those of skill in the art are familiar with various techniques for positioning a patient to facilitate access to a spinal disc space from a lateral approach. This knowledge includes making adjustments as needed to provide access around the iliac crest for lateral access to the lumbo-sacral spine. Thus, this description will be brief and should be considered exemplary rather than limiting to the teachings of the present disclosure.

A patient may be positioned in a lateral decubitus position on a radiolucent breaking table. The patient may be stabilized and secured to the table with surgical tape:
  A) just below the iliac crest
  B) over the thoracic region;
  C) from the iliac crest to the knee, then secured to the table; and
  D) from the table to the knee, past the ankle, then secured back to the table.

Placing the table break at the iliac crest may work well when targeting the L3/L4 or L4/L5 disc spaces. When targeting the L1/L2 or the L2/L3 disc spaces it may be helpful to position the patient so that the table break is cephalad of the iliac crest. After positioning, a true Anterior/Posterior (A/P) image may be obtained of the targeted disc using a C-arm imaging device (not shown). Likewise a true lateral image may be obtained using the C-arm imaging device. A line in the anterior/posterior direction may be drawn on the patient to represent the midline of the targeted disc. Additional lines may be added to represent the front, back, and midline of the disc space in the lateral direction.

After conventional draping and preparation of the surgical site, a table mounted retractor arm (not shown) may be mounted to the table for use later in the process.

Access to Psoas.

Make an anterior-to-posterior incision over the center marking of the disc space. This incision may be 35 to 40 millimeters in length for some patients. The incision may be transverse, vertical, or oblique depending on preference.

Using finger or blunt dissection, open the incision down to fascia over the external oblique muscles. Incise fascia in line with the muscle fibers. Continue blunt or finger dissection through the muscle layers into the retroperitoneal space to the psoas muscle. After blunt or finger dissection has made a pathway to the psoas muscle, the access channel may be enlarged through conventional techniques such as a sequence of one or more dilation tubes of increasing diameter and decreasing length. The term enlarge is meant to include the various processes known in the art to increase the volume of an opening. This would include dilation, dissection, retraction, or combinations thereof, and analogous actions.

Depth indications on the outermost dilator may be used to select a channel retractor. For example the first outermost dilator has depth markings for 100 millimeters, 120 millimeters and 140 millimeters on one side along the longitudinal shaft of the outermost dilator. The surgeon notes the value of the marker closest to the patient's skin and selects a corresponding channel retractor (discussed below) to insert over the outer surface of the outermost dilator. The channel retractor is advanced distally down to the psoas muscle and then secured with the table mounted retractor arm with a stabilization arm. All of the tissue dilators are removed and a lateral fluoroscopic image is obtained to confirm placement of the channel retractor is centered over the targeted disc space. If the channel retractor is not centered, adjustments are made so that the channel retractor is positioned directly over the targeted disc.

Figure 8:
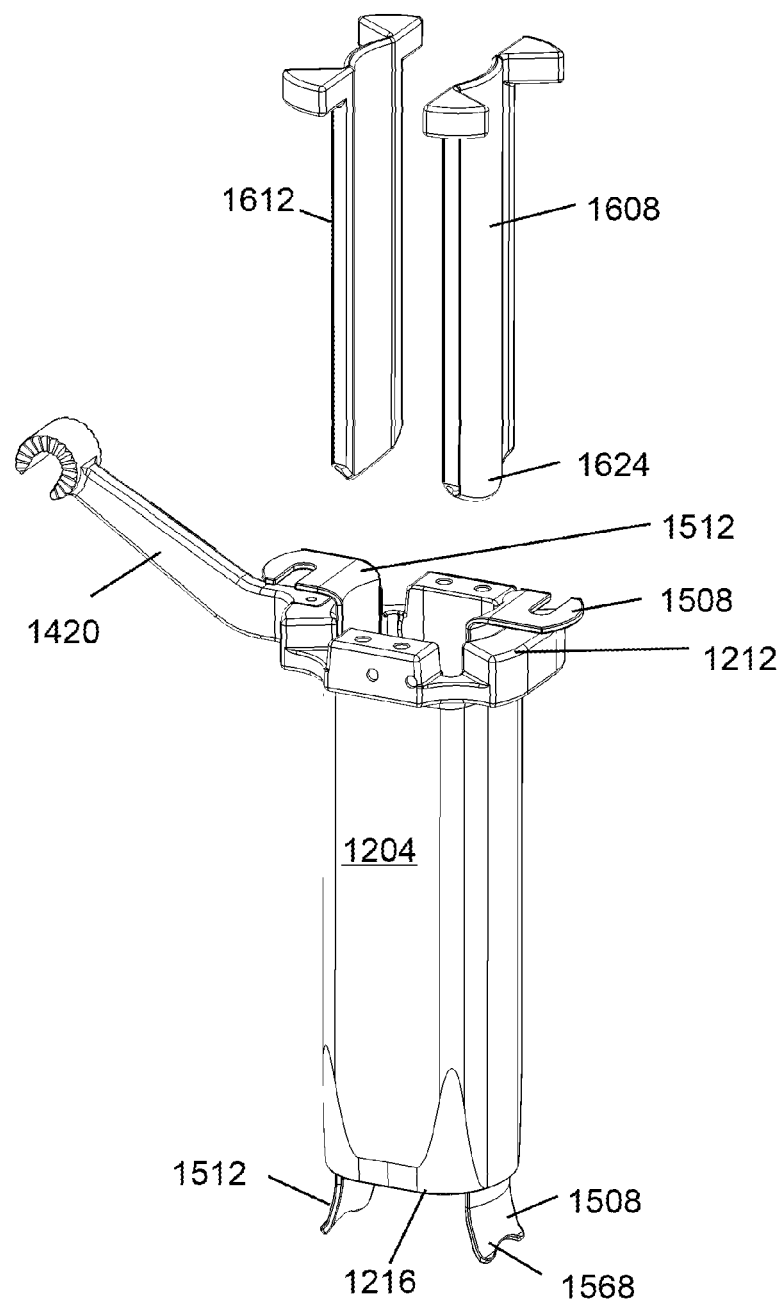
FIG. 8 shows a perspective view of channel retractor with a pair of extended retractors and a pair of slide gates.

FIG. 8 shows channel retractor 1204. The channel retractor 1204 may be connected to the operating table via one or more stabilizer arm 1420. A pair of extended retractors 1508 and 1512 is shown protruding above the proximal end 1212 of the channel retractor 1204 and beyond the distal end 1216 of the channel retractor 1204. The extended retractors 1508 and 1512 are shown without their removable handles which would be attached when manipulating the extended retractors 1508 and 1512 and then optionally removed to minimize obstructions near the proximal end 1212 of the channel retractor 1204. FIG. 16 of U.S. Pat. No. 8,795,167 provides an example of removable handles.

A pair of slide gates 1608 and 1612 is shown in this figure but would not be present until they were in use. As discussed in detail below, once one or both extended retractors 1508 and 1512 are placed with their distal end portions 1568 into a slit in the psoas or other relevant tissue, the distal ends 1624 of slide gates 1608 and 1612 may be inserted into gate tracks 1254 (not shown here) in the channel retractor 1204 to force the extended retractors 1508 and 1512 radially outward from the longitudinal centerline of a lumen running through the channel retractor 1204. This controlled outward pressure on the relevant extended retractor 1508 or 1512 from the paired slide gate 1608 or 1612 will increase as the slide gate (1608 or 1612) is inserted deeper into the gate track 1254 in the channel retractor 1204.

Alternatively, once one or both extended retractors 1508 and 1512 are placed with their distal end portions 1568 in place to move tissue, the surgeon may use the distal end portion 1568 to move the tissue and then use the relevant slide gate 1608 or 1612 to hold the extended retractor 1508 or 1512 and engaged tissue out of the way of the extended access channel extending beyond the distal end 1216 of the channel retractor 1204.

Note that one slide gate 1608 or 1612 may be introduced and inserted partway or fully into the track of the channel retractor 1204. Then the other slide gate 1608 or 1612 may be inserted into the track of the channel retractor 1204. Thus, at any one time, the surgeon need only address the position of one extended retractor 508 or 1512 and one slide gate 1608 or 1612 as the channel retractor 1204 is affixed to the surgical table via one or more stabilizer arms 1420.

Note that the surgeon does not need to wait until both slide gates 1608 and 1612 are positioned in the relevant tracks of the channel retractor 1204, before pushing down on both slide gates 1608 and 1612 so that pressure is applied at the same time to both extended retractors 1508 and 1512 to force open the slit in the psoas muscle or other tissue. Rather, the surgeon may insert an extended retractor (1508 or 1512) and then achieve a half split of the psoas by inserting the relevant slide gate 1608 or 1612. The process may be repeated with the second extended retractor 1508 or 1512 and the second slide gate 1608 or 1612 to achieve a full split of the psoas muscle.

An alternative is to have the surgeon apply force to one or the pair of extended retractors 1508 and 1512 to force the psoas tissue open and then use the slide gates 1608 and 1612 only to retain the extended retractors 1508 and 1512 against the interior perimeter walls of the channel retractor 1204.

Figure 9:
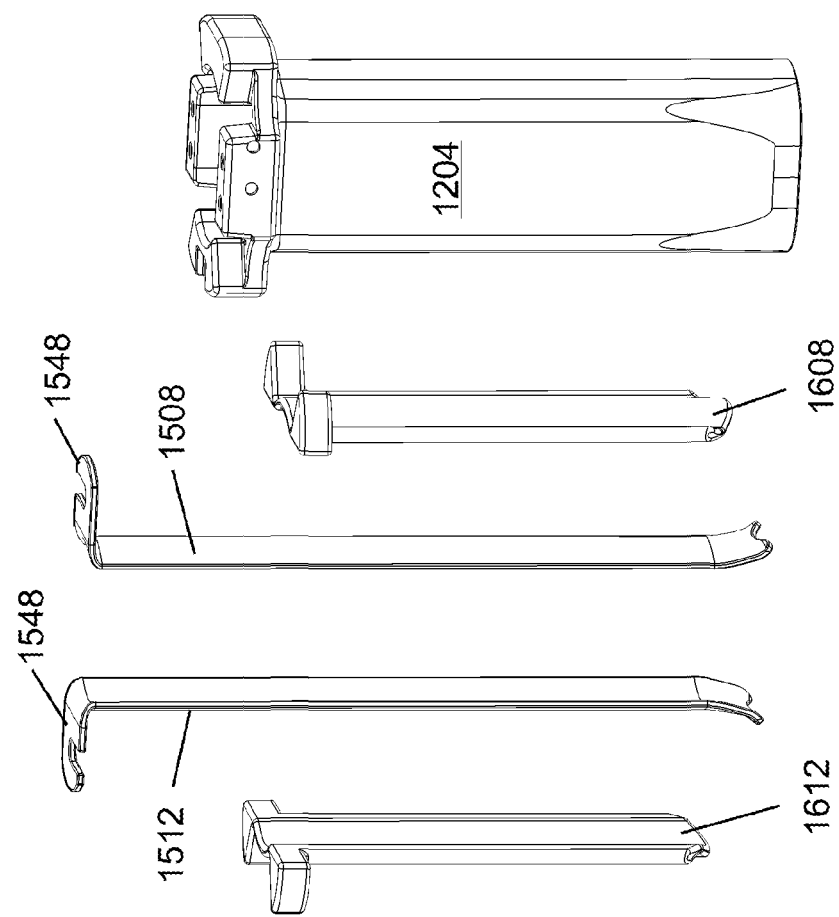
FIG. 9 shows a perspective view of the major components to provide a sense of relative size.

FIG. 9 shows a perspective view of the major components to provide a sense of relative size. The extended retractors 1508 and 1512 are longer than the channel retractor 1204 as the extended retractors 1508 and 1512 extend beyond both the proximal end 1212 of the channel retractor 1204 and the distal end 1216 of the channel retractor 1204 in order to hold tissue away from a longitudinal centerline of the extended access channel.

The slide gates 1608 and 1612 are shorter than the channel retractor 1204 but may be close to the length of the channel retractor 1204.

Figure 10:
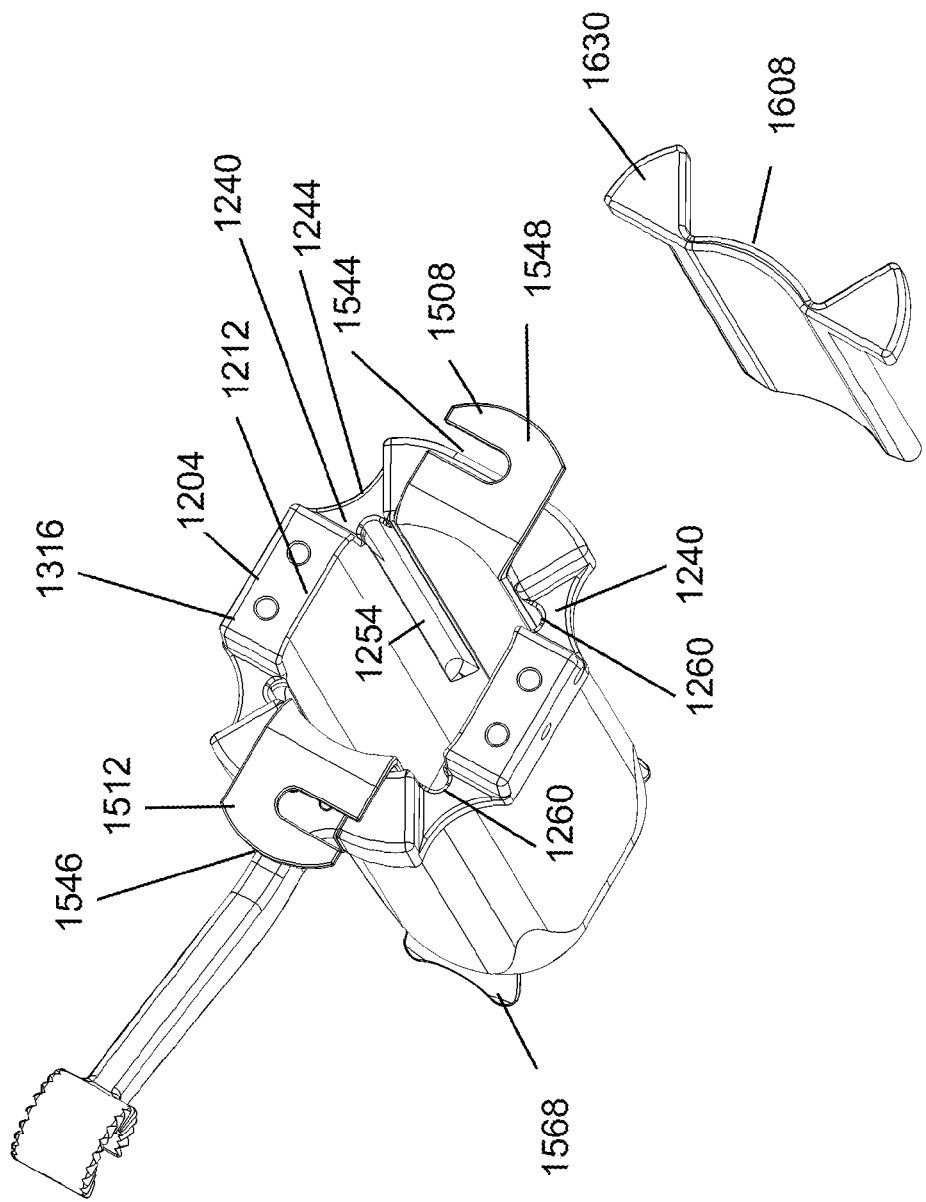
FIG. 10 shows a top perspective view of the channel retractor, extended retractors and, and a slide gate.

FIG. 10 shows a top perspective view of the channel retractor 1204, extended retractors 1508 and 1512, and a slide gate 1608. Each of the extended retractors 1508 and 1512 has a lateral gap 1544 in the horizontal portions 1548 (best seen in FIG. 9). Although the lateral gaps 1544 are not required for use of the teachings of the present disclosure, the lateral gaps 1544 in the horizontal portions 1548 allow a removable handle (not shown here) to reversibly engage the extended retractors 1508 and 1512 so that the removable handle may be removed when not needed to reduce the number of items extending in the work area around the proximal end 1212 of the channel retractor 1204. The lateral gap 1544 could be replaced with a radial gap that extends inward from the extreme end 1546 of the horizontal portion 1548 of each of the extended retractors 1508 and 1512 provided that an appropriate removable handle is adapted to engage the radial gaps.

Slide gate 1608 has a pair of tabs 1630 which fit into corresponding openings (tab gaps 1240) in the proximal end 1212 of the channel retractor so that a fully inserted slide gate 1608 or 1612 does not extend above the proximal face 1316 of the channel retractor 1204. The tabs 1630 serve as stops to prevent over travel during insertion of a slide gate 1608 or 1612.

Each tab gap 1240 has an outer edge 1244. The outer edge 1244 is selected so that the tab 1630 when seated in the tab gap 1240 extends laterally beyond the outer edge 1244 so that a user can push upward on the tab 1630 to lift the tab 1630 up and out of the tab gap 1240 to remove the slide gate 1608 or 1612 from the channel retractor 1204.

Visible in FIG. 10 are the outer ends 1260 of the gate tracks 1254 that receive the slide gates 1608 and 1612.

Figure 11:
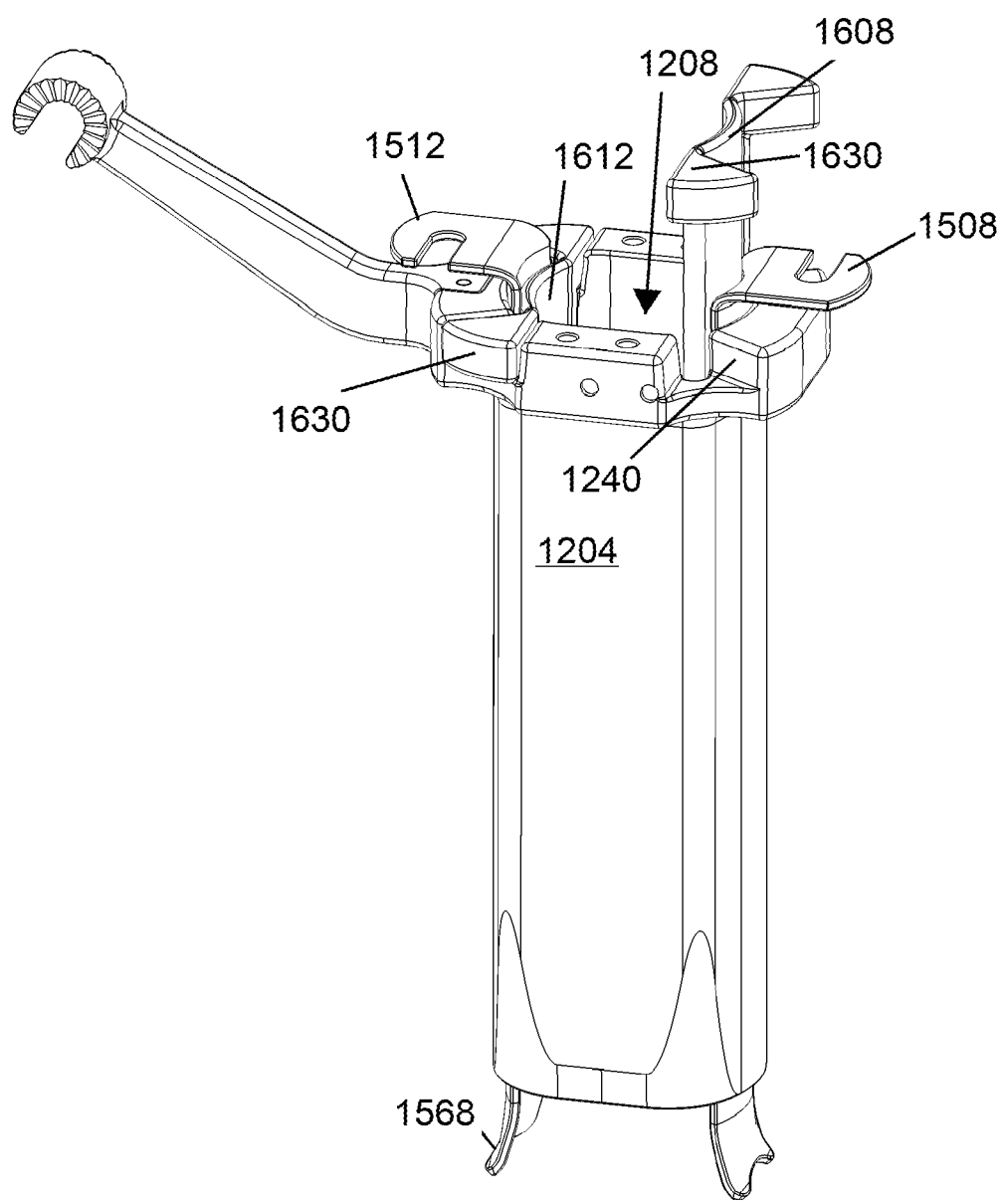
FIG. 11 shows a front, right, top perspective view of a channel retractor.

FIG. 11 shows a front, right, top perspective view of a channel retractor 1204. Slide gate 1612 is fully inserted into channel retractor 1204 so that the tabs 1630 are fully inserted into tab gaps 1240. The distal end portion 1568 of extended retractor 1512 is held out away from the centerline of the lumen that runs through the channel retractor 1204.

Slide gate 1608 is partially inserted into gate track 1254 (best seen in FIG. 10). Tabs 1630 on slide gate 1608 are not yet seated in tab gaps 1240. A working channel 1208 exists between the slide gates 1608 and 1612.

Figure 12:
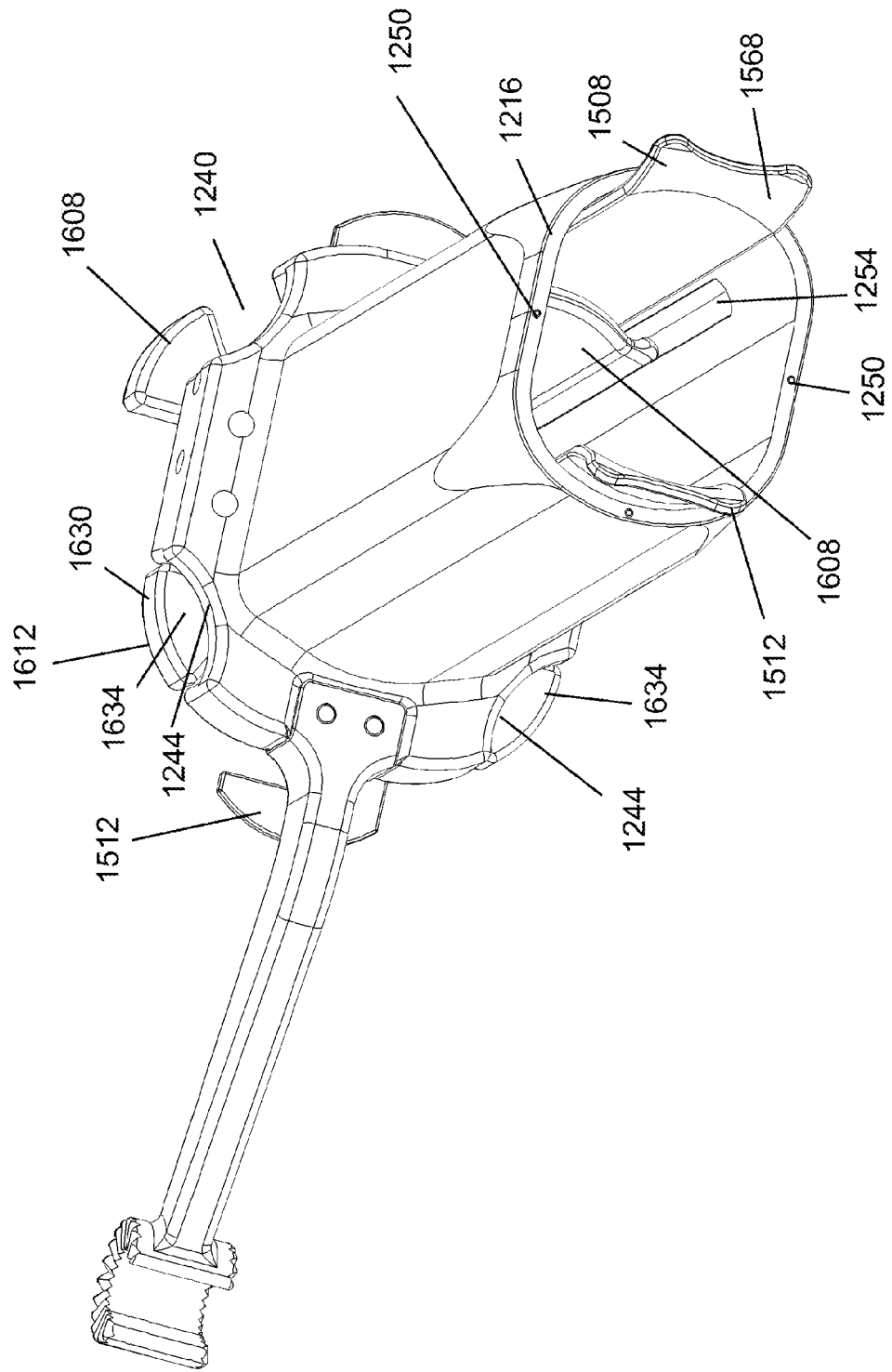
FIG. 12 shows a left, front, bottom perspective view of the assembly from FIG. 11 looking into the distal end of the channel retractor.

FIG. 12 shows a left, front, bottom perspective view of the assembly from FIG. 11 looking into the distal end 1216 of the channel retractor 1204. Slide gate 1612 is fully inserted with tab 1630 inserted into tab gap 1240 but easily removed because the outer edge 1244 of the tab gap 1240 leaves a distal face 1634 of the tab 1630 exposed.

A set of radio-opaque markers 1250 may be placed in the channel retractor 1204. The radio-opaque markers 1250 may be placed on the distal end 1216 of the channel retractor 1204 so that the radio-opaque markers 1250 are visible during fluoroscopy to help envision the placement of the distal end 1216 of the channel retractor 1204 to ensure that the working channel 1208 is aligned with the destination such as a particular disc space between two adjacent vertebrae. A fourth radio-opaque marker 1250 is not visible in FIG. 12 as the fourth radio-opaque marker 1250 is obscured by the distal end of extended retractor 1508.

Figure 13:
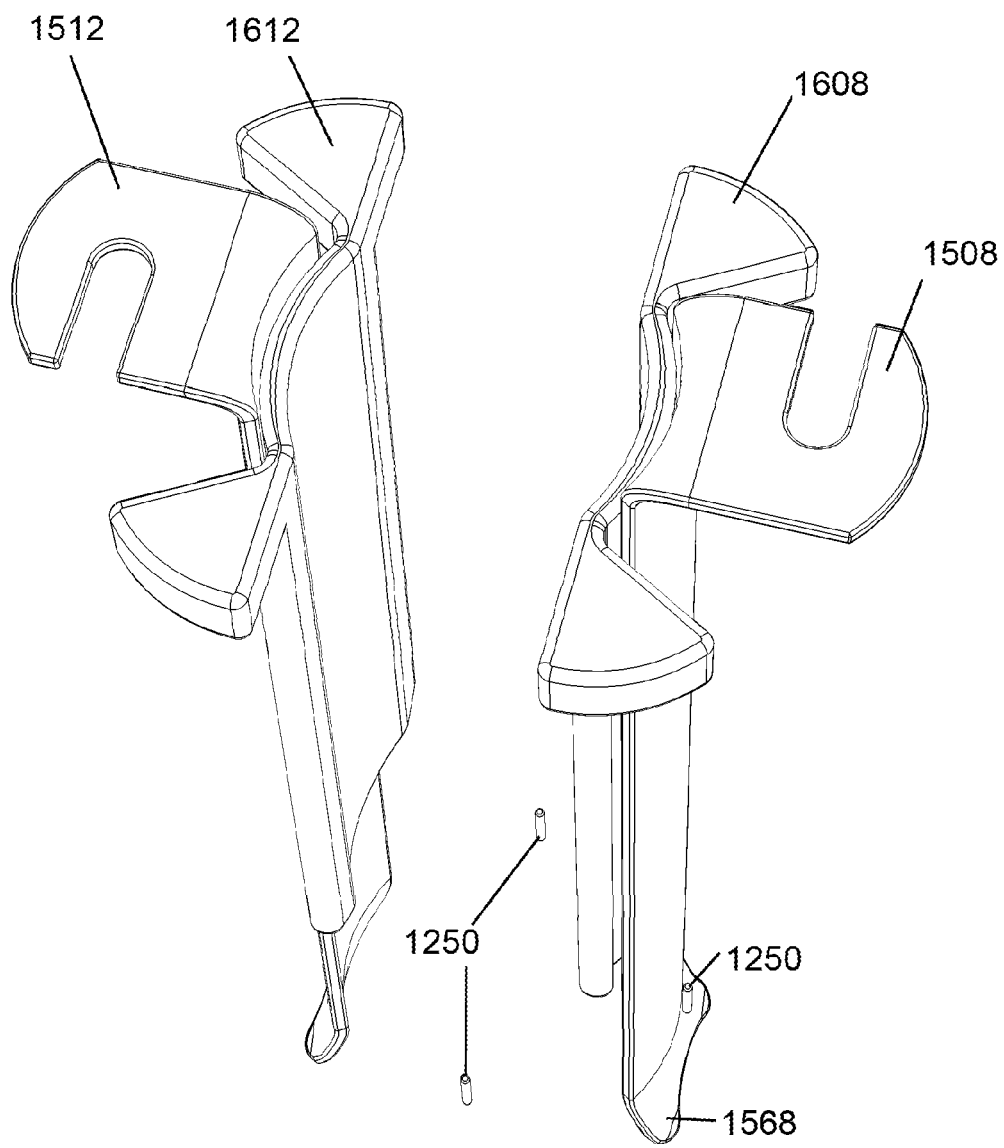
FIG. 13 is a top, front, right perspective view with the channel retractor and stabilizer arm rendered invisible to allow viewing of the extended retractors, slide gates, and some of the radio-opaque markers.

FIG. 13 is provided purely for the purpose of helping to explain the relationship of components in the new access system. FIG. 13 has the channel retractor 1204 and stabilizer arm 1420 rendered invisible to allow an unobstructed view of fully inserted slide gates 1608 and 1612 and the captive extended retractors 1508 and 1512. As indicated by the positions of the radio-opaque markers 1250 which may be embedded in the distal end 1216 of the channel retractor 1204 (rendered invisible), the distal end portions 1568 of the extended retractors 1508 and 1512 extend beyond the distal end 1216 of the channel retractor 1204. The fourth radio-opaque marker is hidden behind the distal end portion 1568 of extended retractor 1512.

Single Retractor Posterior Sweep of Psoas.

The anatomy of the psoas muscle differs from patient to patient and within a single patient, the width of the psoas muscle decreases towards the cephalad end of the psoas muscle. In some instances, a surgeon may prefer to sweep a thin layer of psoas muscle from the anterior side of the channel retractor 1204 to the posterior side of the channel retractor 1204 as this will provide a better clinical solution than attempting to split and work with a relatively thin portion of psoas muscle.

The surgeon would place the distal end portion 1568 of an extended retractor 1508 beyond the distal end 1216 of the channel retractor 1204 to engage an anterior edge of the psoas muscle while the horizontal portion 1548 of the extended retractor extends posteriorly out of the proximal end 1212 of the channel retractor 1204. The surgeon would apply pressure and sweep the distal end portion 1568 and the engaged edge of the psoas muscle posteriorly towards the posterior side of the channel retractor 1204. Once the psoas muscle has been moved, a slide gate 1608 may be engaged in the gate track 1254 on the posterior side of the channel retractor 1204 to retain the psoas muscle.

For surgeries at some levels of the spine, a surgeon may prefer to use two retractors and split the psoas for one patient but later that day may find during a lateral procedure that at the same level of the spine for another patient, it is preferable to use a single retractor posterior sweep. The channel retractor 1204 with a pair of gate tracks 1254 allows this decision to be made after the channel retractor 1204 has been put into place and stabilized by a connection to the operating table.

Mid-Process Adjustments to Maintain a Psoas Split.

Figure 6:
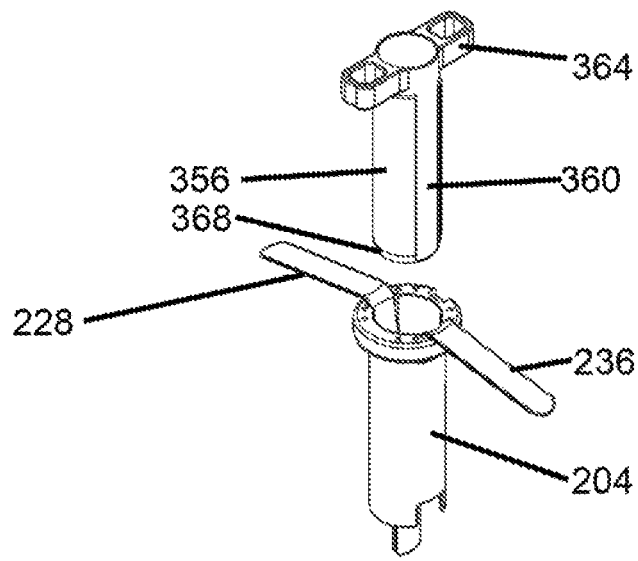
FIG. 6 shows an inner sleeve in proximity to a channel retractor with extended retractors from the prior art.
Figure 7:
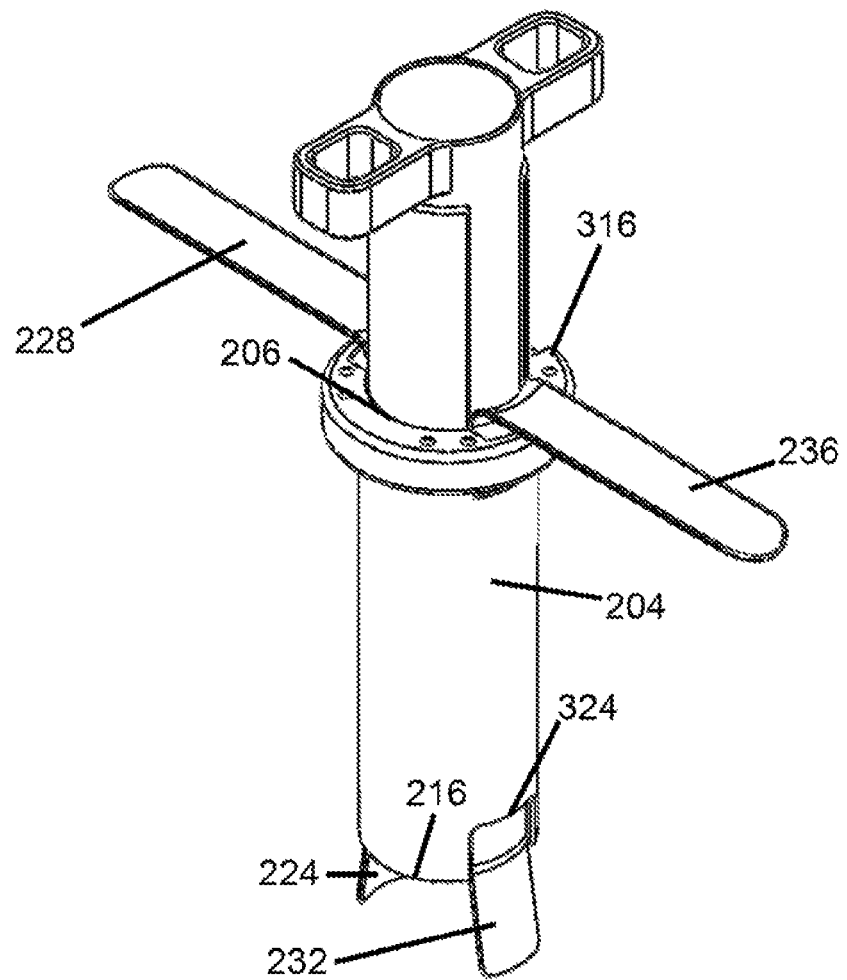
FIG. 7 is a top perspective view during insertion of the inner sleeve to form an assembly from the prior art.

One of the advantages of using a channel retractor 1204 with a pair of gate tracks 1254 and a pair of slide gates 1608 to hold a pair of extended retractors 1508 and 1512 is that mid-procedure a surgeon may release one extended retractor by removing the relevant slide gate 1608 so that the psoas muscle can be swept back out of the way with the extended retractor and then maintained by reinserting the slide gate 1608. For various reasons, there can be muscle creep which causes previously positioned psoas muscle to creep back into the access path. There is an advantage of the individuated control of the extended retractors 1508 and 1512 by individual slide gates 1608 rather than by the use of an inner sleeve (See inner sleeve 356 in FIG. 6) as the use of the inner sleeve results in releasing both extended retractors and allowing the psoas tissue on both sides of the split in the psoas to be released. Once both sides have been released there will again be a need for three hands to hold a pair of extended retractors and insert the inner sleeve to hold the extended retractors away from the extended access channel.

Material Choices.

One choice for material for use in the various channel retractors shown above is medical grade Radel® R5500 (Polyphenylsulfone). This material can withstand sterilization techniques such as Ethylene oxide (EtO) gas, radiation, steam autoclaving, dry heat, and cold sterilization. Other desirable attributes are that the material is dimensionally stable and may be marked with lasers. One of skill in the art will recognize that other materials could be used instead of Radel® R5500. PEEK is another material choice that may be used as it is radiolucent. Composites of carbon fibers and polymers may be selected for creating channel retractors or extended retractors.

Provision of Therapy after Creating an Access Channel.

After creating an access channel first to the psoas muscle then through the psoas muscle using any of the methods described above, a lateral portion of the spine may be accessed for the provision of therapy. One form of therapy is to fuse two adjacent vertebrae together. Some surgeons provide the therapy of spinal fusion without using an implant. Other surgeons use a spinal implant in the process of providing therapy to achieve spinal fusion. Spinal fusion typically involves the use of osteogenic, osteoconductive, or osteoinductive material (bone graft). Bone graft is the material that is used to promote bone growth and forms the scaffold that bridges the adjacent vertebral bodies comprising a motion segment in the spine. Two fused vertebrae do not move with respect to one another.

It is useful to have one name for the variety of materials used to promote fusion. Thus, fusion promoting materials include osteogenic, osteoconductive, and/or osteoinductive material including bone graft material whether the material is autograft or allograft and various bone graft substitutes or bone graft extenders. Various techniques for promoting effective fusion of adjacent vertebrae are well known to those of skill in the art so a minimal summary is sufficient for this document.

Preparation of Disc Space

One process to promote fusion is to conduct a discectomy to remove nucleus pulpous of the disc and to abrade the vertebral endplates adjacent to the disc space as bleeding from the endplates promotes bone growth and fusion. An interbody implant (sometimes called a fusion cage) may be introduced into the disc space along with quantities of a fusion promoting material such as an autograft or any other materials approved for such use. Frequently, the nature of the access channel used to access the disc space will impact the dimensions of the cage that may be delivered to the disc space.

Frequently, tools are inserted that serve as trial implants. These tools provide guidance to the surgeon on the most appropriate size of implant to use for a particular patient's anatomy for a particular access route. The position of the trial implant may be assessed via fluoroscopy. One dimension that may be ascertained by trial devices is the appropriate choice of height for the implant. In some instance it may be that assertive insertion of a series of progressively larger trial devices will serve to increase the distance between adjacent vertebrae (vertebral distraction) which may be a desired outcome of the surgical intervention.

There are other forms of therapies that may be provided to the spine and the methods of providing access set forth above are not limited to the provision of any one particular therapy.

ALTERNATIVES AND VARIATIONS

Non-Interchangeable Slide Gates.

While the disclosure showed the used of interchangeable extended retractors and interchangeable slide gates that fit into the gate tracks on each side of the extended retractor, this is not a requirement of the present disclosure. While those of skill in the art will appreciate that having interchangeable parts reduces certain costs for manufacturing and inventory, it is not a requirement in order to enjoy the benefits of the present disclosure.

Non-Flush Slide Gates.

While the slide gates shown are designed so that when fully inserted the proximal face of the slide gate is not higher than the proximal face of the channel retractor, this is not required. For example the slide gates may not have the tabs 1630 that fit within the tab gap 1240 to facilitate removal of the slide gates. The slide gates may have a handle or a removable handle that is used to remove the slide gates from a fully inserted position into the gate track.

Number and Orientation of Slide Gates.

While the examples set forth above had a channel retractor with a pair of gate tracks located on opposite sides of the channel retractor, this is not a requirement in order to enjoy many of the benefits of the teachings of the present disclosure. While the channel retractor with a single pair of gate tracks to hold a pair of extended retractors with a pair of slide gates is well suited for maintaining a split in the psoas muscle, other surgical procedures may find that other arrangements of extended retractors and slide gates in gate tracks are useful for maintaining an extended access channel. An extended retractor may have four gate tracks to afford the surgeon an option to decide mid-procedure whether to use one pair of gate tracks on opposite sides of the channel retractor or use another set of gate tracks rotated 90 degrees from the first pair to allow tissue to be retained in one of two orientations.

It may be useful to use more than two extended retractors to hold back tissue for certain surgical approaches, perhaps with larger diameter channel retractors so a set of gate tracks may be provided in a channel retractor to allow three, four, or more extended retractors to be used and retained to maintain an extended access channel.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

The legal limitations of the scope of the claimed invention are set forth in the claims that follow and extend to cover their legal equivalents. Those unfamiliar with the legal tests for equivalency should consult a person registered to practice before the patent authority which granted this patent.

What is claimed is:

1. An assembly for maintaining an extended access channel in tissue, the assembly comprising:
    a channel retractor having:
        a lumen from an opening at a proximal end of the channel retractor to an opening at a distal end of the channel retractor; the lumen providing a first portion of an access channel;
        a longitudinal centerline of the lumen;
        a first gate track to receive a slide gate to press an extended retractor radially outward relative to the longitudinal centerline of the lumen;
    a first extended retractor with:
        a proximal portion that extends out of the proximal end of the channel retractor;
        a distal portion that extends out of the distal end of the channel retractor; and
        an intermediate portion between the proximal portion and the distal portion; and
    a first slide gate adapted to fit within the first gate track to retain the first extended retractor between the first slide gate and the channel retractor and thus maintain the first extended retractor away from the longitudinal centerline of the lumen;
        such that when the first extended retractor has the distal portion extending beyond the distal end of the channel retractor for retaining tissue to provide the extended access channel,
        inserting the first slide gate into the first gate track causes the distal portion of the first extended retractor to remain separated from the longitudinal centerline of the lumen to maintain the extended access channel.

2. The assembly for maintaining an extended access channel of claim 1 wherein the channel retractor has at least one tab gap in a proximal face of the channel retractor to receive a corresponding tab from the first slide gate when the first slide gate is fully inserted into the first gate track so that a surgeon may subsequently pull on a distal face of the tab to remove the first slide gate from the channel retractor.

3. The assembly for maintaining an extended access channel of claim 1 wherein the channel retractor has a second gate track to receive a slide gate to press an extended retractor radially outward relative to the longitudinal centerline of the lumen; and the assembly further comprising:
    a second extended retractor with:
        a proximal portion that extends out of the proximal end of the channel retractor;
        a distal portion that extends out of the distal end of the channel retractor; and
        an intermediate portion between the proximal portion and the distal portion;
    a second slide gate adapted to fit within the second gate track to retain the second extended retractor radially outward from the longitudinal centerline of the lumen;
        such that when the first extended retractor and the second extended retractor have at least parts of their distal portions extending beyond the distal end of the channel retractor and inserted into an opening in tissue, inserting the first slide gate and second slide gates into the first gate track and second gate track causes the distal portions of the first extended retractor and the second extended retractor to remain separated from the longitudinal centerline of the lumen which may be used to maintain the opening in tissue distal to the distal end of the channel retractor.

4. The assembly of claim 3 wherein the second gate track is located opposite from the first gate track.

5. The assembly of claim 3 wherein the second gate track is not located opposite from the first gate track.

6. The assembly of claim 3 wherein there are at least three gate tracks.

7. The assembly of claim 3 wherein the assembly is adapted such that when the first extended retractor and the second extended retractor have at least parts of their distal portions inserted into an opening in tissue, inserting the first slide gate and the second slide gate sufficiently into the first gate track and the second gate track causes the distal portions of the first extended retractor and the second extended retractor to move outward relative to the longitudinal centerline of the lumen enlarging the opening in tissue distal to the distal end of the channel retractor.

* * * * *